(12) United States Patent
Fawzy et al.

(10) Patent No.: US 8,784,886 B2
(45) Date of Patent: Jul. 22, 2014

(54) COATING CAPSULES WITH ACTIVE PHARMACEUTICAL INGREDIENTS

(75) Inventors: Abdel Fawzy, Somerville, NJ (US); George Bobotas, Tarpon Springs, FL (US)

(73) Assignee: GlaxoSmithKline, LLC, Wilmington, DE (US)

( * ) Notice: Subject to any disclaimer, the term of this patent is extended or adjusted under 35 U.S.C. 154(b) by 963 days.

(21) Appl. No.: 11/716,020

(22) Filed: Mar. 9, 2007

(65) Prior Publication Data

US 2007/0212411 A1   Sep. 13, 2007

Related U.S. Application Data

(60) Provisional application No. 60/780,306, filed on Mar. 9, 2006, provisional application No. 60/840,012, filed on Aug. 25, 2006, provisional application No. 60/851,294, filed on Oct. 13, 2006, provisional application No. 60/856,832, filed on Nov. 6, 2006, provisional application No. 60/880,441, filed on Jan. 16, 2007.

(51) Int. Cl.
*A61K 9/48* (2006.01)
*A61K 9/64* (2006.01)
*A61K 9/52* (2006.01)

(52) U.S. Cl.
USPC .......................... 424/463; 424/456; 424/457

(58) Field of Classification Search
USPC ......................................... 424/456, 457, 463
See application file for complete search history.

(56) References Cited

U.S. PATENT DOCUMENTS

| | | | |
|---|---|---|---|
| 4,670,287 A | 6/1987 | Tsuji | |
| 4,816,259 A * | 3/1989 | Matthews et al. | 424/463 |
| 5,013,569 A * | 5/1991 | Rubin | 426/585 |
| 5,502,077 A | 3/1996 | Breivik et al. | 514/560 |
| 5,641,512 A | 6/1997 | Cimiluca | |
| 5,656,667 A | 8/1997 | Breivik et al. | 514/560 |
| 5,698,594 A | 12/1997 | Breivik et al. | 514/560 |
| 6,159,993 A | 12/2000 | Seed et al. | |
| 6,235,311 B1 * | 5/2001 | Ullah et al. | 424/472 |
| 6,284,268 B1 | 9/2001 | Mishra et al. | |
| 6,350,468 B1 | 2/2002 | Sanso | |
| 6,531,150 B1 | 3/2003 | Sunohara et al. | |

(Continued)

FOREIGN PATENT DOCUMENTS

| DE | 199 30 030 A1 | 1/2001 |
|---|---|---|
| EP | 1 529 524 B1 | 5/2005 |

(Continued)

OTHER PUBLICATIONS

Belluzzi, A. et al., "Pharmacokinetic Study of a New Coated Fish Oil Derivative (PURPEA) in a Group of Crohn's Disease Patients," Gastroenterology, vol. 102, No. 4, Part 2, 1992, p. A542.

(Continued)

*Primary Examiner* — Aradhana Sasan
(74) *Attorney, Agent, or Firm* — Loretta J. Sauermelch; Alan X. Scrivner

(57) ABSTRACT

Pharmaceutical compositions in unit dose form comprising capsules containing one or more first active pharmaceutical ingredient in a pharmaceutically acceptable vehicle, coated with one or more second active pharmaceutical ingredients, wherein the unit dose form is a pharmaceutical grade finished dosage form, and methods of making and using the same.

21 Claims, 1 Drawing Sheet

(56) References Cited

U.S. PATENT DOCUMENTS

| | | |
|---|---|---|
| 6,572,885 B2 | 6/2003 | Oshlack et al. |
| 6,632,451 B2 | 10/2003 | Penhasi et al. |
| 6,720,001 B2 | 4/2004 | Chen et al. |
| 7,022,713 B2 | 4/2006 | Aoki et al. |
| 7,109,206 B2 | 9/2006 | Seed et al. |
| 7,153,538 B2 | 12/2006 | Brown et al. |
| 7,642,287 B2 | 1/2010 | Guzman et al. |
| 8,367,725 B2 | 2/2013 | Yokoyama et al. |
| 2004/0018248 A1* | 1/2004 | Bendich .................... 424/682 |
| 2004/0043070 A1 | 3/2004 | Ayres |
| 2004/0224020 A1* | 11/2004 | Schoenhard .............. 424/471 |
| 2006/0222701 A1 | 10/2006 | Kulkarni et al. |
| 2007/0036862 A1* | 2/2007 | Rongen et al. ............ 424/472 |
| 2007/0191467 A1 | 8/2007 | Rongen et al. ............ 514/423 |
| 2007/0196465 A1* | 8/2007 | Bobotas et al. .......... 424/456 |
| 2008/0085911 A1 | 4/2008 | Rongen et al. ............ 514/275 |
| 2009/0012167 A1 | 1/2009 | Rongen et al. ............ 514/560 |
| 2009/0239927 A1 | 9/2009 | Bobotas et al. .......... 514/423 |
| 2010/0010026 A1 | 1/2010 | Rongen et al. ............ 514/275 |
| 2011/0294841 A1 | 12/2011 | Guzman et al. |
| 2013/0065956 A1 | 3/2013 | Yokoyama et al. |

FOREIGN PATENT DOCUMENTS

| | | | |
|---|---|---|---|
| JP | 59-157018 | 9/1984 | |
| WO | WO 95/14460 A1 | 6/1995 | |
| WO | WO 96/10996 A1 | 4/1996 | |
| WO | WO 99/06035 | 2/1999 | |
| WO | WO 99/22719 | 5/1999 | |
| WO | WO 99/47123 | 9/1999 | |
| WO | WO 02/43659 * | 6/2002 | |
| WO | WO 2005/013940 A1 | 2/2005 | |
| WO | WO 2006/013602 | 2/2006 | |
| WO | WO2006/017692 A2 | 2/2006 | |
| WO | WO 2006/062748 | 6/2006 | ........... A61K 31/426 |
| WO | WO 2006/096806 | 9/2006 | ........... A61K 31/401 |
| WO | WO 2007/011886 A2 | 1/2007 | |
| WO | WO 2007/016256 A2 | 2/2007 | |
| WO | WO 2006/045865 | 7/2007 | |
| WO | WO 2007/103557 | 9/2007 | ........... A61K 31/397 |
| WO | WO 2008/045170 | 4/2008 | ........... A61K 31/401 |
| WO | WO 2008/045465 | 4/2008 | ........... A61K 31/20 |
| WO | WO 2008/088415 | 7/2008 | ........... A01N 43/36 |

OTHER PUBLICATIONS

Belluzzi, Andrea, M.D. et al., "Effect of an Enteric-Coated Fish-Oil Preparation on Relapses in Crohn's Disease," The New England Journal of Medicine, vol. 334, No. 24, Jun. 13, 1996, pp. 1557-1560.

Reich, Gabriele, "Formulation and physical properties of soft capsules," Pharmaceutical Capsules, Second Edition, Chapter 11, 2004, pp. 201-212.

Yuksel, N. Enhanced bioavailability of piroxicam using Gelusire 44/14 and Labrasol: in vitro and in vivo evaluation. European J. Pharmaceutics and Biopharmaceutics. 2003, vol. 56, pp. 453-459, see entire document.

Biju, S.S. Dual coated erodible microcapsules for modified release of diclofenac sodium. European J. Pharmaceutics and Biopharmaceutics. 2004, vol. 58, pp. 61-67, see entire document.

* cited by examiner

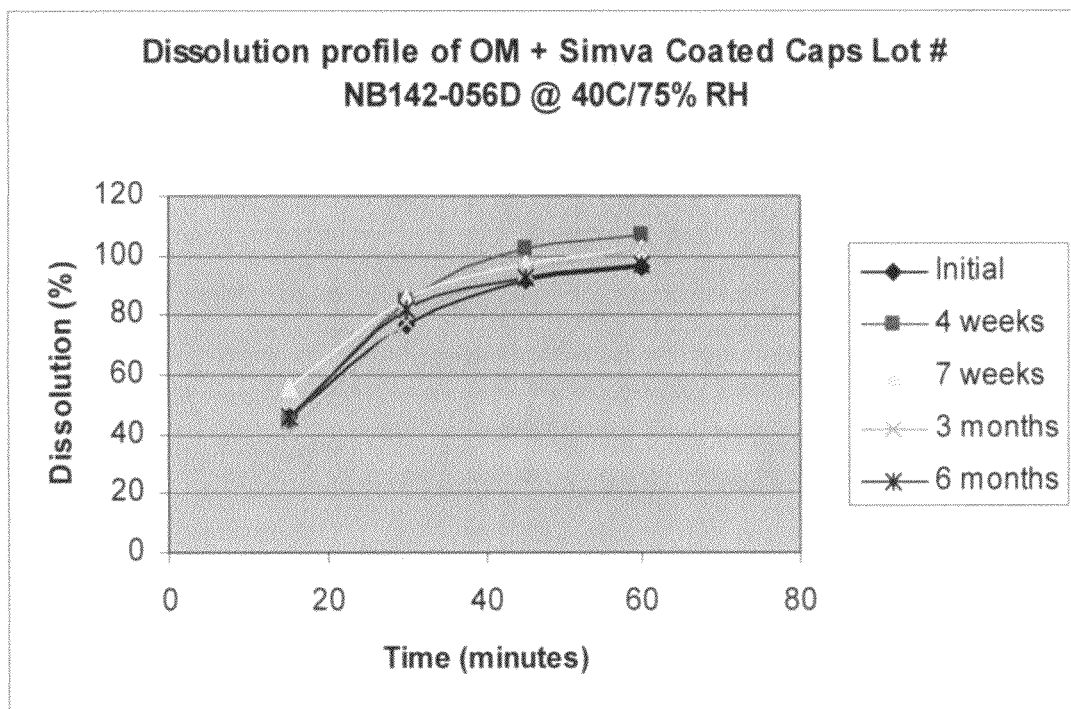

COATING CAPSULES WITH ACTIVE PHARMACEUTICAL INGREDIENTS

The present application claims priority from U.S. Provisional Application Ser. Nos. 60/780,306, filed Mar. 9, 2006; 60/840,012, filed Aug. 25, 2006; 60/851,294, filed Oct. 13, 2006; 60/856,832, filed Nov. 6, 2006; and 60/880,441, filed Jan. 16, 2007; and U.S. patent application Ser. Nos. 11/488,181, filed Jul. 18, 2006; and Ser. No. 11/494,799, filed Jul. 28, 2006. Each application is hereby incorporated by reference in its entirety.

FIELD OF THE INVENTION

The present invention relates, generally, to pharmaceutical compositions in unit dose form comprising hard or soft capsules containing at least one first active pharmaceutical ingredient in a pharmaceutically acceptable vehicle, wherein the capsule is coated with at least one coating having at least one second active pharmaceutical ingredient and the unit dose form is a pharmaceutical grade finished dosage form, and methods of making the same.

DESCRIPTION OF THE RELATED ART

The formulation of drugs into capsules, for example soft or hard gelatin capsules, has been reported to solve many problems associated with tableting. Improved stability has also been achieved through the use of gelatin capsules, most notably with active pharmaceutical ingredients (APIs) which are highly susceptible to oxidation and hydrolysis. An example is USP vitamin A which is relatively unstable in air and light; however, the encapsulated contents show no significant loss of potency for 3 years or longer when stored and packaged under the prescribed conditions of temperature and humidity. In addition, the bioavailability of hydrophobic APIs can be significantly increased when formulated into gelatin capsules.

Fixed dose API combinations offer several advantages. The advantages of these preparations are convenience, avoidance of potential mistakes made possible by too many APIs given on the same day, possible synergetic effect and lower prices. However, in some cases, combining two or more APIs in a capsule formulation can result in chemical incompatibilities, which may be the result of oxidation-reduction, acid-base, hydrolysis, transesterification, or combination reactions. And in some other cases, it may also affect the bioavailability of one or more components of the formulation.

Coating APIs on a soft capsule has heretofore not been commercially feasible, because content uniformity is especially difficult with coatings on soft capsules, due to the low surface roughness of the capsule shell and the intrinsic solubility of the shell components in water, and with oblong-shaped capsules, as it is difficult to obtain a uniform coating on the edges or axial regions of the capsule (versus the equatorial regions). See, for example, the reference to by Reich (2004), "Chapter 11: Formulation and physical properties of soft capsules," Pharmaceutical Capsules, 2d Ed., Pharmaceutical Press, 201-212, which is incorporated by reference in its entirety.

U.S. Pat. No. 4,670,287, U.S. Pat. No. 6,572,885, and PCT Application Publication No. WO 95/14460, generally disclose, in passing, embodiments in which capsules containing solid pharmaceutical formulations may be coated with a coating including an API.

U.S. Patent Application Publication No. 2006/0222701 discloses capsules with a hydrophobic inner layer and at least one hydrophilic outer layer, where the hydrophobic inner layer may include a hydrophilic component such as an API which may be fully or partially encapsulated, or part of an adsorption complex.

U.S. Pat. No. 5,641,512 discloses an analgesic encapsulated in a soft gelatin capsule, wherein a xanthine derivative, such as caffeine, is embedded in the capsule shell itself.

U.S. Pat. No. 6,350,468 discloses a double capsule where an internal capsule is placed inside an external one, and where each internal and external capsule includes one or more APIs.

Several references disclose enteric capsules containing omega-3 fatty acids. U.S. Pat. No. 6,531,150 discloses enteric capsules having a buffer layer of a water-soluble gel containing an acid or acid salt between the content of omega-3 fatty acids and the gelatin-based coating layer. European Patent Application No. EP 1529524 and German Application No. DE19930030 disclose gelatin capsules containing omega-3 fatty acids coated with xylose to provide resistance to gastric juice and increase stability. Belluzi et al., N. Eng. J. Med. (1996) 334 (24): 1557-60, and Belluzi et al., Gastroenterology (1992) 102(4) pt. 2: A542, each disclose enteric coated fish oil capsules (PUREPA® Tillotts-Pharma) for delayed delivery.

U.S. Pat. No. 6,632,451 broadly discloses a two-pulse gastrointestinal delivery system having a swellable core comprising one or more active agents and an outer coat comprising one or more active agents, where the outer coat is separated from the core by an inner coat having water-insoluble hydrophilic particulate matter embedded water-insoluble carrier such that the particulate matter form channels in the inner coat in the presence of aqueous liquids that interconnect the core with the outer surface of the inner coat until the core swells and breaks the inner coat. Meanwhile, U.S. Patent Application Publication No. 2004/0043070 broadly discloses a substrate coated by fluid bed method with a molten coating material containing an antigen or pharmaceutical agent or drug and less then 10% solvent.

U.S. Pat. No. 7,153,538 discloses methods of coating a pharmaceutical substrate with an active coating material, where the active coating material is preferably applied electrostatically. U.S. Pat. No. 7,153,538 also discloses that conventional spray coating techniques (such as the tumble coating method) are "not appropriate for use where accuracy in the amount of the active material applied to the cores is required because there is little control over the amount of coating material applied to each core."

U.S. Patent Application Publication No. 2004/0224020 discloses an oral dosage form with active agents in controlled cores and in immediate release gelatin capsule coats.

Japanese Patent Application Publication No. JP 59-157018 discloses capsules filled with an edible oil having a medicinal effect and coated with a powder having a medicinal effect.

There is an unsatisfied need in the art for pharmaceutical grade finished dosage forms of capsules containing a first API, especially soft capsules and/or oblong-shaped capsules, and coated with one or more coats wherein at least one coat includes at least one second API, and for methods of making the same.

SUMMARY OF THE INVENTION

Embodiments of the present invention are directed to a pharmaceutical composition in unit dose form comprising: a hard or soft capsule comprising at least one first active pharmaceutical ingredient (API) in a pharmaceutically acceptable vehicle and optionally a solubilizer; and one or more coatings on the capsule, wherein at least one coating comprises at least one second API; and wherein the unit dose form is a pharmaceutical grade finished dosage form.

In some embodiments, additional coatings on the capsules, such as immediate release coatings, protective coatings, enteric or delayed release coatings, sustained release coatings, barrier coatings, and combinations thereof may be placed between the capsule and the at least one coating comprising the at least one second API. In some embodiments, the capsules may be coated with at least one top coating on the at least one coating comprising the at least one second API, and may include, but are not limited to, immediate release coatings, protective coatings, enteric or delayed release coatings, sustained release coatings, barrier coatings, and combinations thereof.

In cases of chemical incompatibilities or undesired changes in the bioavailability of a fixed dose drug combination formulation, coating a capsule with one of the APIs combines the advantages of a fixed drug combination delivery system with the elimination of the incompatibility experienced between the APIs.

One or more of the APIs of the present invention may also be formulated with a combination of one or more inactive ingredients including, but not limited to, solubilizers, antioxidants, chelating agents, buffers, emulsifiers, thickening agents, dispersants, and preservatives.

BRIEF DESCRIPTION OF THE DRAWING

FIG. 1 discloses a comparative dissolution profile of the simvastatin coated soft gelatin capsules containing omega-3 fatty acids of Example 2, after storage at various times at 40° C./75% RH.

DETAILED DESCRIPTION OF THE INVENTION

Embodiments of the present invention are directed to pharmaceutical compositions in unit dose form comprising a hard or soft capsule comprising at least one first API in a pharmaceutically acceptable vehicle, and one or more coatings on the capsule, wherein at least one coating comprises at least one second API, and wherein the unit dose form is a pharmaceutical grade finished dosage form.

The manufacture of hard or soft capsules is generally known by those of ordinary skill in the art. For example, soft capsules may be made by various processes including the plate process, the rotary die process, the reciprocating die process, and the continuous process. See, for example, Ebert (1978), "Soft Elastic Gelatin Capsules: A Unique Dosage Form," *Pharmaceutical Technology* 1(5); Reich (2004), "Chapter 11: Formulation and physical properties of soft capsules," Pharmaceutical Capsules, 2d Ed., Pharmaceutical Press, 201-212, hereby incorporated by reference in their entireties. See also, U.S. Pat. No. 5,478,508 and U.S. Pat. No. 5,882,680, incorporated by references herein in their entireties, disclosing methods of manufacturing seamless capsules. Examples of the capsular materials include, but are not limited to, natural or synthetic gelatin, pectin, casein, collagen, protein, modified starch, polyvinyl pyrrolidone, acrylic polymers, cellulose derivatives (such as, but not limited to, hydroxypropyl methylcellulose (HPMC)), and combinations thereof, optionally with one or more plasticizers and/or water. Capsular materials may also include one or more preservatives, coloring and opacifying agents, flavorings and sweeteners, sugars, gastroresistant substances, or combinations thereof.

The shape and size of the capsules can vary in accordance with the invention. The shape of the capsule may be, but is not limited to, round, oval, tubular, oblong, twist off, or a non-standard shape (e.g., a fish, tree, star, heart, or bear), preferably oblong. The size of the capsule used will vary in accordance to the volume of the fill composition intended to be contained therein.

For example, in some embodiments of the present invention, hard or soft gelatin capsules may be manufactured in accordance with conventional methods as a single body unit comprising the standard capsule shape. A single-body soft gelatin capsule typically may be provided, for example, in sizes from 3 to 22 minims (1 minimim being equal to 0.0616 ml) and in shapes of oval, oblong or others. The gelatin capsule may also be manufactured in accordance with conventional methods, for example, as a two-piece hard gelatin capsule, sealed or unsealed, typically in standard shape and various standard sizes, conventionally designated as (000), (00), (0), (1), (2), (3), (4), and (5). The largest number corresponds to the smallest size. Non-standard shapes may be used as well. In some embodiments, the hard or soft gelatin capsule may contain powder, beads or microtablets (e.g., similar system to U.S. Pat. No. 5,681,588, incorporated herein by reference in its entirety), instead of or in addition to the pharmaceutically acceptable vehicle.

The terms "first API" and "second API" include single as well as multiple (i.e., more than one) API. For example, the second API may comprise more than one API applied in one or more coating layers. The first API and second API may be the same or different. Optional additional coatings on the capsules may be provided between the shell of the capsule and the coating comprising the second API and/or on and/or between coatings of the second API.

In some embodiments, APIs from which the first API and/or the second API, which are the same or different, may be independently selected from include, but are not limited to, the following: analgesics, anti-inflammatory agents, anti-helminthics, anti-arrhythmic agents, anti-asthma agents, anti-bacterial agents, anti-viral agents, anti-coagulants, anti-dementia agents, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-thyroid agents, anti-tussives, anxiolytics, sedatives, hypnotics, neuroleptics, neuroprotective agents, β-blockers, cardic inotropic agents, cell adhesion inhibitors, corticosteroids, cytokine receptor activity modulators, diuretics, anti-Parkinson's agents, gastrointestinal agents, histamine H-receptor antagonists, keratolytics, lipid regulating agents, muscle relaxants, nitrates and other anti-anginal agents, non-steroid anti-asthma agents, nutritional agents, opioid analgesics, sex hormones, stimulants and anti-erectile dysfunction agents.

In some preferred embodiments, the first API and/or the second API comprises a lipid regulation agent such as, but not limited to, fatty acids such as omega-3 fatty acids, sterol or stanol fatty acid esters, a statin compound, a squalene synthesis inhibitor, an azetidinone-based cholesterol absorption inhibitor, a LDL (low density lipoprotein) catabolism enhancer, a peroxisome proliferator-activated receptor (PPAR) agonist and/or antagonist, niacin and derivatives such as nicotinamide, a bile acid sequestrant, an MTP inhibitor, an LXR agonist and/or antagonist, and combinations thereof.

In a preferred embodiment, the first API itself is present in the form of a pharmaceutically acceptable vehicle, i.e., the pharmaceutically acceptable vehicle has pharmaceutical properties and is used, in whole or in part, as fill for the hard or soft capsule. Particularly preferred first APIs in this embodiment are selected from omega-3, omega-5, omega-6, omega-7, or omega-9 fatty acids, or sterol or stanol fatty acid esters. In such cases, the pharmaceutically acceptable vehicle is typically (but not necessarily) present in the form of an oil, and there is no need for additional ingredients to provide the pharmaceutically acceptable vehicle. Such additional ingredients, however, may of course be included with the first API in such embodiments. Thus, as used herein, the phrase "at least one first active pharmaceutical ingredient in a pharmaceutically acceptable vehicle" includes the first API alone when the first API itself is present in the form of a pharmaceutically acceptable vehicle.

The sterol fatty acid ester may include one or more of sitosterol, campesterol, stigmasterol, avenasterol, brassicasterol, ergosterol, and lanosterol, and the stanol fatty acid ester may include one or more of cholestanol, sitostanol, campestanol, stigmastanol, avenastanol, brassicastanol, ergostanol, and lanostanol. The fatty acid ester is selected from a methyl ester, n-propyl ester, iso-propyl ester, n-butyl ester, iso-butyl ester, sec-butyl ester, and tert-butyl ester. In a preferred embodiment, the fatty acid ester is an ethyl ester. The esters may be linear, branched, saturated, unsaturated, or polyunsaturated, and may be modified with functional groups including halo, ester, ether, keto, amino, nitrile, carboxy, imino, thio, oxo, cyano, thiocyano, and nitro. The alcohol can be a primary, secondary or tertiary alcohol.

As used herein, the term "omega-3 fatty acids" includes natural or synthetic omega-3 fatty acids, or pharmaceutically acceptable esters, derivatives, conjugates (see, e.g., Zaloga et al., U.S. Patent Application Publication No. 2004/0254357, and Horrobin et al., U.S. Pat. No. 6,245,811, each hereby incorporated by reference), precursors or salts thereof and mixtures thereof. Examples of omega-3 fatty acid oils include but are not limited to omega-3 polyunsaturated, long-chain fatty acids such as a eicosapentaenoic acid (EPA), docosahexaenoic acid (DHA), and α-linolenic acid; esters of omega-3 fatty acids with glycerol such as mono-, di- and triglycerides; and esters of the omega-3 fatty acids and a primary, secondary or tertiary alcohol such as fatty acid methyl esters and fatty acid ethyl esters. Preferred omega-3 fatty acid oils are long-chain fatty acids such as EPA or DHA, triglycerides thereof, ethyl esters thereof and mixtures thereof. The omega-3 fatty acids or their esters, derivatives, conjugates, precursors, salts and mixtures thereof can be used either in their pure form or as a component of an oil, such as fish oil, preferably purified fish oil concentrates. Commercial examples of omega-3 fatty acids suitable for use in the invention include Incromega F2250, F2628, E2251, F2573, TG2162, TG2779, TG2928, TG3525 and E5015 (Croda International PLC, Yorkshire, England), and EPAX6000FA, EPAX5000TG, EPAX4510TG, EPAX2050TG, K85TG, K85EE, K80EE and EPAX7010EE (Pronova Biocare a.s., 1327 Lysaker, Norway).

Some embodiments includes omega-3 fatty acids in the capsule in a concentration of at least 40% by weight, preferably at least 50% by weight, more preferably at least 60% by weight, still more preferably at least 70% by weight, most preferably at least 80% by weight, or even at least 90% by weight. Preferably, the omega-3 fatty acids comprise at least 50% by weight of EPA and DHA, more preferably at least 60% by weight, still more preferably at least 70% by weight, most preferably at least 80%, such as about 84% by weight. The omega-3 fatty acids may comprise about 5 to about 100% by weight, more preferably about 25 to about 75% by weight, still more preferably about 40 to about 55% by weight, and most preferably about 46% by weight of EPA. The omega-3 fatty acids may comprise about 5 to about 100% by weight, more preferably about 25 to about 75% by weight, still more preferably about 30 to about 60% by weight, and most preferably about 38% by weight of DHA. All percentages above are by weight as compared to the total fatty acid content in the capsule, unless otherwise indicated. The percentage by weight may be based on the free acid or ester forms, although it is preferably based on the ethyl ester form of the omega-3 fatty acids even if other forms are utilized in accordance with the present invention. Preferably, the EPA and DHA are in a weight ratio of EPA:DHA of from 99:1 to 1:99, preferably from 1:4 to 4:1, more preferably from 1:3 to 3:1, and most preferably from 1:2 to 2:1. The omega-3 fatty acids may also comprise pure EPA or pure DHA.

The most preferred form of omega-3 fatty acids is OMACOR® omega-3 fatty acids, as described in U.S. Pat. Nos. 5,502,077, 5,656,667 and 5,698,594, hereby incorporated by reference in their entireties, (K85EE, Pronova Biocare A.S., Lysaker, Norway) and preferably comprises the following characteristics (per dosage form):

| Test | Minimum Value | Maximum Value |
| --- | --- | --- |
| Eicosapentaenoic acid C20:5 | 430 mg/g | 495 mg/g |
| Docosahexaenoic acid C22:6 | 347 mg/g | 403 mg/g |
| EPA and DHA | 800 mg/g | 880 mg/g |
| Total n − 3 fatty acids | 90% (w/w) | |

The omega-3 fatty acid composition optionally includes chemical antioxidants, such as alpha tocopherol, oils, such as soybean oil and partially hydrogenated vegetable oil, and lubricants such as fractionated coconut oil, lecithin and a mixture of the same.

In preferred embodiments of the invention, the first API comprises omega-3 fatty acids.

Statin compounds are drugs that lower blood cholesterol levels by inhibiting hydroxymethylglutalyl CoA (HMG-CoA) reductase. Examples of preferred statin compounds include pitavastatin, pravastatin, simvastatin, lovastatin, atorvastatin, fluvastatin and salts thereof, more preferably simvastatin.

Squalene synthesis inhibitors are drugs that lower blood cholesterol levels by inhibiting the synthesis of squalene. An example of a preferred squalene synthesis inhibitor includes (S)-alpha-Bis(2,2-dimethyl-1-oxopropoxy)methoxy-phosphinyl-3-phenoxybenzenebutanesulfonic acid mono potassium salt (BMS-188494).

Azetidinone-based compounds can be inhibitors of cholesterol absorption. Examples of azetidinone-based cholesterol absorption inhibitors include ezetimibe or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug. Another preferred azetidinone-based cholesterol absorption inhibitor is the phenolic glucuronide of ezetimibe or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug. Two other ezetimibe related analogs and cholesterol absorption inhibitors for use in the present invention, for example, are referred to in the literature as: 1) SCH 58053 or (+)-7-(4-chlorophenyl)-2-(4-flourophenyl)-7-hydroxy-3R-(4-hydroxyphenyl)-2-azaspiro[3,5]nonan-1-one) (see J. Lipid Res. 43:1864-1873(2002))

and 2) SCH 48461 or (3R)-3Phenylpropyl)-1,(4S)-bis(4-methoxyphenyl)-2-azetidinone (see J. Med. Chem., 41:973-980 (1998)).

LDL catabolism enhancers are drugs that lower blood cholesterol levels by increasing the number of LDL (low-density lipoprotein) receptors. Examples of the LDL catabolism enhancers include, but are not limited to, the compounds described in Japanese Patent Application No. 117(1995)-316144, which is incorporated by reference herein in its entirety, and represented by the formula:

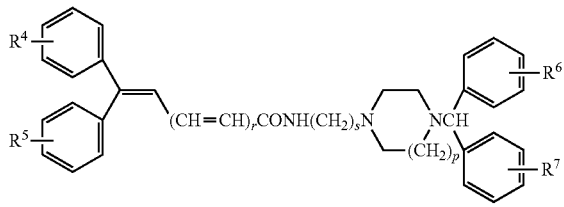

wherein $R^4$, $R^5$, $R^6$ and $R^7$ are the same or different, and represent hydrogen atom, a halogen atom, a lower alkyl group or a lower alkoxy group; r is 0-2; s is 2-4; p is 1-2; or a salt thereof; specifically N-[2-[4-bis(4-fluorophenyl)methyl-1-piperazinyl]ethyl]-7,7-diphenyl-2,4,6-heptatrienic acid amide, etc.

PPAR agonists and/or antagonists include, but are not limited to, for example, PPAR-alpha, PPAR-gamma, PPAR-delta, PPAR-beta, and combinations of two or more of these types. Some PPAR agonists and/or antagonists may work by one or more mechanism and, therefore, may be characterized as belonging to more than one or all types (e.g., PPAR-alpha gamma agonists and/or antagonists, PPAR-gamma delta agonists and/or antagonists, and panagonists (i.e., PPAR agonists and/or antagonists active against all types of receptors)).

PPAR-alpha agonists include fibrate compounds, and are drugs that lower blood cholesterol levels by inhibiting the synthesis and secretion of triglycerides in the liver and activate a lipoprotein lipase. Examples of preferred fibrate compounds include bezafibrate, beclobrate, binifibrate, ciplofibrate, clinofibrate, clofibrate, clofibric acid, etofibrate, fenofibrate, fenofibric acid, gemfibrozil, nicofibrate, pirifibrate, ronifibrate, simfibrate, theofibrate and combinations thereof, preferably fenofibrate.

PPAR-gamma agonists and/or antagonists include, for example, thiazolidinediones (such as troglitazone (e.g., REZULIN®), pioglitazone (e.g., ACTOS®), and rosiglitazone (e.g., AVANDIA®). Other PPAR-gamma agonists include, for example FK-614 (Astellas), rivoglitazone (Sankyo), AMG 131 (Amgen), R483 (Roche), T131 (Tularik Inc.), and partial PPAR-gamma agonists and/or antagonists, such as metaglidasen and MBX-2044 (Metabolex).

PPAR-alpha/gamma agonists and/or antagonists include, for example, some non-thiazolidinediones (such as tesaglitazar (e.g., GALIDA®), naviglitizar and muraglitazar (e.g., PARGLUVA®), TAK-564 (Takeda), AVE 0847, AVE 0897, and AVE 5376 (Sanofi-Aventis), AZD 6610 (AstraZeneca), E-3030 (Eisai), R1439 (Roche)), and JTT-501 and JTP-20604 (Japan Tobacco).

PPAR agonists and/or antagonists active against all types of receptors (i.e., panagonists) may include, for example, 677954 (GlaxoSmithKline), netoglitazone (Perlegen Sciences), and PLX204 (Wyeth/Plexxikon).

In other preferred embodiments of the invention, the first API and/or the second API, preferably the second API, comprises an antiarrhythmic agent, which preferably may include any of the following: class Ia antiarrhythmic agents (for example, quinidine (e.g., QUINIDEX®), procainamide (e.g., PRONESTYL®), and disopyramide (e.g., NORPACE®); class Ib antiarrhythmic agents (for example, lidocaine (e.g., XYLOCAINE®), mexiletine (e.g., MEXITIL®), tocainide (e.g., TONOCARD®), and phenyloin); class Ic antiarrhythmic agents (for example, encainide (e.g., ENKAID®), flecainide (e.g., TABOCOR®), moricizine and propafenone (e.g., RHYTHMOL®)); class II antiarrhythmic agents (for example, esmolol (e.g., BREVIBLOC®), propranolol (e.g., INDERAL®), acebutolol (e.g., SECTRAL®), sotalol (e.g., BETAPACE®), and metoprolol (TOPROL-XL® or LOPRESSOR®); class III antiarrhythmic agents (for example, amiodarone (e.g., CORDARONE®), azimilide, bretylium, clofilium, dofetilide, tedisamil, ibutilide, sematilide, dronaderone, RSD-1235, and sotalol (e.g., BETAPACE®)); class IV antiarrhythmic agents (for example, verapamil (e.g., CALAN® or ISOPTIN®), mibefradil (e.g., POSICOR®) and diltiazem (e.g., CARDIZEM®)); and class V antiarrhythmic agents (for example, adenosine (e.g., ADENOCARD®) and digoxin (e.g., LANOXIN®)). Other potential antiarrhythmic agents in accordance with the invention may include GYKI-16638, CPU-86017, EGIS-7229, KCB-328, L-768673, RWJ-28810, NIP-151, NS-1643, KB-R7943, ATI-2001, AL-275, Cardiostem, KMUP-880708, SLV-316, TY-10835, AZD-1305, CLN-93, PQ-1006, SAR-114646, S-2646, XEN-501, CVT-3619, TRC-30X, AVE-1231, DL-017, PJ-875, pirmenol, moracizine, pilsicainide, nifekalant, dexsotalol, landiolol, nifedipine, ATI-2042, AVE-0118, nibentan, stobadine, YM-758, SSR-149744, rotigaptide, tedisamil, and tecadenoson. In a preferred embodiment, the antiarrhythmic agent include class Ic, preferably propafenone and/or flecainide, and/or class III antiarrhythmic agents, preferably amiodarone, azilimilide, dronaderone, RSD-1235, sotalol, ibutilide, dofetilide, and/or other antiarrhythmic agents such as ATI-2042, AVE-0118, nibentan, stobadine, YM-758, SSR-149744, rotigaptide, tedisamil, and/or tecadenoson.

In other preferred embodiments of the invention, the first API and/or the second API, preferably the second API, comprises at least one non-steroidal anti-inflammatory drug (NSAID). In more preferred embodiments, the NSAIDs include any of the following: ibuprofen, naproxen, ketoprofen, oxaprozin, diclofenac, indomethacin, sulindac, piroxicam, meclofenamate, mefanamic acid, nabumetone, etoldolac, ketorolac, choline magnesium trisalicylate, aspirin, diflunisal, salsalate, fenoprofen, flurbiprofen, pirprofen, tiaprofenic acid, loxoprofen, indoprofen, fenbufen, carprofen, suprofen, celecoxib, valdecoxib, rofecoxib, parecoxib, deracoxib, lumiracoxib, etoricoxib or meloxicam.

In yet other preferred embodiments of the invention, the first API and/or the second API, preferably the second API, comprises at least one dihydropyridine calcium channel blocker, such as but not limited to, dotarizine, Bay K 8644, amlodipine (e.g., Norvasc®), felodipine (e.g., Plendil®), lacidipine (e.g., Lacipil®), lercanidipine (e.g., Zanidip®), nicardipine (e.g., Cardene®), nifedipine (e.g., Adalat®, Procardia®), nimodipine (e.g., Nimotop®), nisoldipine (e.g., Sular®), nitrendipine and isradipine (e.g., DynaCirc®). Preferably, the dihydropyridine calcium channel blocker comprises isradipine.

In still other preferred embodiments of the invention, the first API and/or the second API, preferably the second API, comprises at least one anti-epileptic agent, such as but not limited to, phenobarbital, phenyloin, ethosuximide, carbamazepine, valproic acid, divalproic acid, felbamate, gabapentin, lamotrigine, topiramate, tiagabine, levetiracetam, oxcarbazepine, zonisamide, pregabalin, vigabatrin, primidone, and benzodiazepines such as: clonazepam, lorazepam, diazepam, clobazam, alprazolam, oxazepam, temazepam, triazolam, chlordiazepoxide, flurazepam, nitrazepam, estazolam, flunitrazepam, halazepam, ketazolam, loprazolam, lormetazepam, medazepam, midazolam, nordazepam, phenazepam, pinazepam, prazepam, quazepam, and tetrazepam.

In other preferred embodiments of the invention, the first API and/or the second API, preferably the second API, comprises at least one anti-Parkinson's agent, such as but not limited to, carbidopa, levodopa, entacapone, bromocriptine, pergolide, pramipexole, ropinirole, apomorphine, trihexyphenidyl, benztropine, biperiden, ethopropazine, selegiline, rasagiline, tolcapone, amantadine, diphenhydramine, and procyclidine.

In some embodiments of the present invention, the first API and the second API may be present in a range of about 1:1000 to about 1000:1 by weight, preferably about 200:1 to about 200:1 by weight. In some embodiments, the first API may be present in an amount from about 1 mg to about 3000 mg, more preferably from about 10 mg to about 2000 mg. In some embodiments, the second API may be present in an amount from about 1 mg to about 1000 mg, more preferably from about 5 mg to about 500 mg, and even more preferably from about 5 mg to about 100 mg.

In some preferred embodiments the first API comprises about 500 mg to about 2000 mg of omega-3 fatty acids, preferably about 1000 mg of omega-3 fatty acids.

In some preferred embodiments, the second API comprises about 1 mg to about 150 mg of a statin compound, preferably about 5 mg to about 100 mg of a statin compound.

In some preferred embodiments, the second API comprises about 1 mg to about 300 mg of a fibrate compound, preferably about 10 to about 100 mg of a fibrate compound.

The term "pharmaceutically acceptable vehicle," as used herein, includes any of the following: a solution where the first API and optional other ingredients are wholly dissolved in a solubilizer (e.g., a pharmaceutically acceptable solvent or mixture of solvents), wherein the solution remains in clear liquid form at about room temperature; a suspension; an oil; or a semi-solid, wherein the first API and optionally other ingredients are dissolved wholly or partially in a solubilizer (e.g., an emulsion, cream, etc.).

A "pharmaceutical grade finished dosage form" as used herein may be construed as a unit dose form suitable for administration to, for example, human or animal subjects, and having content uniformity acceptable to regulatory authorities. For example, under the USP requirements for content uniformity, a pharmaceutical grade finished dosage form should have an amount of API within the range of 85% to 115% of the desired dosage and an RSD less than or equal to 6.0%. In addition, a pharmaceutical grade finished dosage form must be stable (i.e., have a "shelf life") for a pharmaceutically acceptable duration of time, preferably at least six months, more preferably at least one year, and most preferably at least two years, when stored at room temperature (about 23° C. to 27° C., preferably about 25° C.) and 60% relative humidity. Typically, stability is determined by physical appearance and/or chemical modification of the ingredients, in accordance with standards well-known in the pharmaceutical arts.

Embodiments of the present invention can be applied to fixed dosage forms wherein the APIs are incompatible with one another. For example, the incompatibility may be a physical incompatibility or a chemical incompatibility. Physical incompatibility is often called pharmaceutical incompatibility and is evidenced by the failure of the APIs to combine properly. Chemical incompatibility generally occurs when APIs react chemically upon combination to alter the composition of one or more of the ingredients. Manifestations of incompatibility include insolubility of one agent in another agent or a vehicle (physical), immiscibility of two or more liquids (physical), precipitation due to changes in solubility of the medium ("salting out") (physical), liquification of solids mixed in a dry state (physical), cementation of insoluble ingredients in liquid mixtures (physical), change in color (chemical), oxidative or reductive reactions (chemical), precipitation due to chemical reaction (chemical), inactivation or decomposition (chemical), etc. Physical incompatibility may be determined by visual inspection, e.g. with or without magnification against a background, and chemical incompatibility may be measured e.g. by a stability-indicating HPLC assay, gas chromatography/mass spectroscopy (GC/MS), or other means known in the art.

The first API is contained in the capsule. In certain embodiments, the first API is combined with a solubilizer. Solubilizers include surfactants, hydrophilic or hydrophobic solvents, oils or combinations thereof.

One type of solubilizer that may be used is a vitamin E substance. This group of solubilizers includes a substance belonging to the group of $\alpha$-, $\beta$-, $\gamma$-, $\delta$-, $\zeta 1$-, $\zeta 2$- and $\eta$-tocopherols, their dl, d and l forms and their structural analogues, such as tocotrienols; the corresponding derivatives, e.g., esters, produced with organic acids; and mixtures thereof. Preferred vitamin E substance solubilizers include tocopherols, tocotrienols and tocopherol derivatives with organic acids such as acetic acid, propionic acid, bile acid, lactic acid, pyruvic acid, oxalic acid, malic acid, malonic acid, succinic acid, maleic acid, fumaric acid, tartaric acid, citric acid, benzoic acid, cinnamic acid, mandelic acid, polyethylene glycol succinate and salicylic acid. Particularly preferred vitamin E substance solubilizers include alpha-tocopherol, alpha-tocopheryl acetate, alpha-tocopheryl acid succinate, alpha-tocopheryl polyethylene glycol 1000 succinate and mixtures thereof.

Another group of solubilizers are monohydric alcohol esters of organic acids. The monohydric alcohol can be, for example, ethanol, isopropanol, t-butanol, a fatty alcohol, phenol, cresol, benzyl alcohol or a cycloalkyl alcohol. The organic acid can be, for example, acetic acid, propionic acid, butyric acid, a fatty acid of 6-22 carbon atoms, bile acid, lactic acid, pyruvic acid, oxalic acid, malic acid, malonic acid, succinic acid, maleic acid, fumaric acid, tartaric acid, citric acid, benzoic acid, cinnamic acid, mandelic acid and salicylic acid. Preferred solubilizers in this group include trialkyl citrates, lower alcohol fatty acid esters and lactones. Preferred trialkyl citrates include triethyl citrate, acetyltriethyl citrate, tributyl citrate, acetyltributyl citrate and mixtures thereof with triethyl citrate being particularly preferred. Particularly preferred lower alcohol fatty acid esters include ethyl oleate, ethyl linoleate, ethyl caprylate, ethyl caprate, isopropyl myristate, isopropyl palmitate and mixtures thereof. Lactones may also serve as a solubilizer. Examples include $\epsilon$-caprolactone, $\delta$-valerolactone, $\beta$-butyrolactone, isomers thereof and mixtures thereof.

The solubilizer may be a nitrogen-containing solvent. Preferred nitrogen-containing solvents include dimethylformamide, dimethylacetamide, N-alkylpyrrolidone, N-hydroxyalkylpyrrolidone, N-alkylpiperidone, N-alkylcaprolactam and mixtures thereof wherein alkyl is a $C_{1-12}$ branched or straight chain alkyl. Particularly preferred nitrogen-containing solvents include N-methyl 2-pyrrolidone, N-ethyl 2-pyrrolidone or a mixture thereof. Alternatively, the nitrogen-containing solvent may be in the form of a polymer such as polyvinylpyrrolidone.

Another group of solubilizers includes phospholipids. Preferred phospholipids include phosphatidylcholine, phosphatidylethanolamine, phosphatidylserine, phosphatidylinositol, lecithins, lysolecithins, lysophosphatidylcholine, polyethylene glycolated phospholipids/liysophospholipids, lecithins/lysolecithins and mixtures thereof.

Another group of solubilizers are glycerol acetates and acetylated glycerol fatty acid esters. Preferred glycerol acetates include acetin, diacetin, triacetin and mixtures thereof, with triacetin being particularly preferred. Preferred acetylated glycerol fatty acid esters include acetylated monoglycerides, acetylated diglycerides and mixtures thereof.

In addition, the solubilizer may be a glycerol fatty acid ester. The fatty acid component is about 6-22 carbon atoms. The glycerol fatty acid ester can be a monoglyceride, diglyceride, triglyceride or mixtures thereof. Preferred glycerol fatty acid esters include monoglycerides, diglycerides, and medium chain triglycerides with fatty acids having about 6-12 carbons and mixtures thereof. Particularly preferred glycerol fatty acid esters include medium chain monoglycerides with fatty acids having about 6-12 carbons, medium chain diglycerides with fatty acids having about 6-12 carbons and mixtures thereof.

The solubilizer may be a propylene glycol ester. Preferred propylene glycol esters include propylene carbonate, propylene glycol monoacetate, propylene glycol diacetate, propylene glycol fatty acid esters, acetylated propylene glycol fatty acid esters and mixtures thereof. Alternatively, the propylene glycol fatty acid ester may be a propylene glycol fatty acid monoester, propylene glycol fatty acid diester or mixture thereof. The fatty acid has about 6-22 carbon atoms. It is particularly preferred that the propylene glycol ester is propylene glycol monocaprylate. Other preferred propylene glycol esters include propylene glycol dicaprylate, propylene glycol dicaprate, propylene glycol dicaprylate/dicaprate and mixtures thereof.

Another group of solubilizers are ethylene glycol esters. Ethylene glycol esters include monoethylene glycol monoacetates, diethylene glycol esters, polyethylene glycol esters and mixtures thereof. Additional examples include ethylene glycol monoacetates, ethylene glycol diacetates, ethylene glycol fatty acid monoesters, ethylene glycol fatty acid diesters, and mixtures thereof. Alternatively, the ethylene glycol ester may be a polyethylene glycol fatty acid monoesters, polyethylene glycol fatty acid diesters or mixtures thereof. Again, the fatty acid component will contain about 6-22 carbon atoms. Particularly preferred ethylene glycol esters are those marketed under the LABRAFIL® and LABRASOL® names.

Hydrophilic solvents which may be used include an alcohol, e.g. a water miscible alcohol, e.g. absolute ethanol, or glycerol. Other alcohols include glycols, e.g. any glycol obtainable from an oxide such as ethylene oxide, e.g. 1,2-propylene glycol. Other examples are polyols, e.g. a polyalkylene glycol, e.g. poly($C_{2-3}$)alkylene glycol. A typical example is a polyethylene glycol. Alternatively the hydrophilic component may preferably comprise an N-alkylpyrolidone, e.g. N—($C_{1-14}$alkyl)pyrolidone, e.g. N-methylpyrolidone, tri($C_{1-4}$alkyl)citrate, e.g. triethylcitrate, dimethylisosorbide, ($C_5$-$C_{13}$)alkanoic acid, e.g. caprylic acid or propylene carbonate.

The hydrophilic solvent may comprise a main or sole component, e.g. an alcohol, e.g. $C_{1-4}$-alcohol, e.g. ethanol, or alternatively a co-component, e.g. which may be selected from partial lower ethers or lower alkanols. Preferred partial ethers are, for example, TRANSCUTOL® (which has the formula $C_2H_5$—[O—($CH_2$)$_2$]$_2$—OH), GLYCOFUROL® (also known as tetrahydrofurfuryl alcohol polyethylene glycol ether), or lower alkanols such as ethanol.

The one or more coatings on the capsule may be applied by any conventional technique including, but not limited to, pan coating, fluid bed coating or spray coating. The coating(s) may be applied, for example, as a solution, suspension, spray, dust or powder.

Embodiments of the present invention provide that at least one coating applied to the outside of the capsule comprises the second API. In some embodiments, the thickness of this layer is sufficient to prevent oxidative degradation of the second API for a pharmaceutically acceptable duration of time. In some embodiments the thickness of this layer is from 5-400 microns, preferably 10-200 microns, more preferably 20-100 microns, most preferably 40-80 microns. In some embodiments, this layer is expressed in terms of percentage weight gain, based on the total weight of the capsule including any layers provided on the capsule prior to the at least one coating comprising the second API. This layer may have a weight gain of 0.05-20%, preferably 0.1-10%, more preferably 0.1-5%, and most preferably 0.25-1%.

Some embodiments of the present invention provide that the at least one coating comprising the second API includes an amount of at least one compound sufficient to prevent oxidative degradation of the at least one second active pharmaceutical ingredient for a pharmaceutically acceptable duration of time. In some embodiments, the at least one compound comprises at least one polymer. The amount of polymer(s) to the amount of the second API is preferably from about 1:20 to about 20:1 by weight, preferably from 1:5 to about 10:1 by weight. In embodiments where the amount of second API is less than about 15 mg, the amount of polymer(s) is preferably from about 1:2 to about 5:1, and more preferably from about 1:1 to about 4:1. In embodiments where the amount of second API is about 20 mg or more, the amount of polymer(s) is preferably about 1:4 to about 4:1, and more preferably about 1:3 to about 2:1. The polymers may include any pharmaceutically acceptable polymers known to those of skill in the art. Preferred polymers include, but are not limited to, cellulose derivatives such as hydroxyethyl cellulose, hydroxypropyl cellulose, hydroxypropyl methylcellulose, polyvinylpyrrolidone, polyvinylpyrrolidone/vinyl acetate copolymer, ethyl cellulose aqueous dispersions and combinations thereof, preferably hydroxypropyl cellulose, ethyl cellulose, and mixtures thereof. The preferred polymers may also include one or more of the polymers disclosed throughout the application or mixtures thereof.

In some embodiments of the present invention, the second API is provided in a coating solution or suspension which is applied to the capsule. In preferred embodiments, the second API is provided in a homogenous coating solution or a heterologous suspension in a pharmaceutically acceptable solvent, preferably an aqueous or organic solvent. Pharmaceutically acceptable organic solvents have the advantages that they may be evaporated or sublimated during production, do not deform, melt, or otherwise change the structure of the capsule (e.g., gelatin in a soft gelatin capsule), and do not generally cause agglomeration of the coated capsules. In preferred embodiments, the pharmaceutically acceptable organic solvent is selected from methanol, ethanol, isopropanol, ethylene glycol, acetone, or mixtures thereof.

Additional pharmaceutically acceptable organic solvents that may be used include, but are not limited to, polypropylene glycol; polypropylene glycol; polyethylene glycol (for example, polyethylene glycol 600, polyethylene glycol 900, polyethylene glycol 540, polyethylene glycol 1450, polyethylene glycol 6000, polyethylene glycol 8000 (all available from Union Carbide), and the like); pharmaceutically acceptable alcohols which are liquids at about room temperature (for example, propylene glycol, ethanol, 2-(2-ethoxyethoxy) ethanol (TRANSCUTOL™, Gattefosse, Westwood, N.J. 07675), benzyl alcohol, glycerol, polyethylene glycol 200, polyethylene glycol 300, polyethylene glycol 400 and the like); polyoxyethylene castor oil derivatives (for example, polyoxyethyleneglycerol triricinoleate or polyoxyl 35 castor oil (CREMOPHOR™ EL, BASF Corp.), polyoxyethyleneglycerol oxystearate (CREMOPHOR™ RH 40 (polyethyleneglycol 40 hydrogenated castor oil) or CREMOPHOR™ RH 60 (polyethyleneglycol 60 hydrogenated castor oil), BASF Corp.), and the like); saturated polyglycolized glycerides (for example, GELUCIRE™ 35/10, GELUCIRE™ 44/14, GELUCIRE™ 46/07, GELUCIRE™ 50/13 or GELUCIRE™ 53/10 and the like, available from Gattefosse, Westwood, N.J.); polyoxyethylene alkyl ethers (for example, cetomacrogol 1000 and the like); polyoxyethylene stearates (for example, PEG-6 stearate, PEG-8 stearate, polyoxyl 40 stearate NF, polyoxyethyl 50 stearate NF, PEG-12 stearate, PEG-20 stearate, PEG-100 stearate, PEG-12 distearate, PEG-32 distearate, PEG-150 distearate and the like); ethyl oleate, isopropyl palmitate, isopropyl myristate and the like; dimethyl isosorbide; N-methylpyrrolidinone; parafin; cholesterol; lecithin; suppository bases; pharmaceutically acceptable waxes (for example, carnauba wax, yellow wax, white wax, microcrystalline wax, emulsifying wax and the like); pharmaceutically acceptable silicon fluids; soribitan fatty acid esters (including sorbitan laurate, sorbitan oleate, sorbitan palmitate, sorbitan stearate and the like); pharmaceutically acceptable saturated fats or pharmaceutically acceptable saturated oils (for example, hydrogenated castor oil (glyceryl-tris-12-hydroxystearate), cetyl esters wax (a mixture of primarily $C_{14}$-$C_{18}$ saturated esters of $C_{14}$-$C_{18}$ saturated fatty acids having a melting range of about 43-47° C.), glyceryl monostearate and the like); and the like.

The coatings may also include a coating material, such as a film forming material and/or binder, and optionally other conventional additives such as lubricants, fillers and antiadherents. Preferred coating materials may include antioxidants, buffers, solubilizers, dyes, chelating agents, disintegrants, and/or absorption enhancers. Surfactants may act as both solubilizers and absorption enhancers. The coating(s) may be formulated for immediate release, delayed or enteric release, or sustained release of the second API in accordance with methods well known in the art. Conventional coating techniques are described, e.g., in *Remington's Pharmaceutical Sciences*, 18th Ed. (1990), hereby incorporated by reference.

Additional coatings to be employed in accordance with the invention may include, but are not limited to, for example, one or more immediate release coatings, protective coatings, enteric or delayed release coatings, sustained release coatings, barrier coatings, and combinations thereof.

An immediate release coating is commonly used to improve product elegance as well as for a moisture barrier, and taste and odor masking. Rapid breakdown of the film in gastric media is important, leading to effective disintegration and dissolution. Eudragit RD100 (Rohm) is an example of such a coating. It is a combination of a water insoluble cationic methacrylate copolymer and a water soluble cellulose ether. In powder form, it is readily dispensable into an easily sprayable suspension that dries to leave a smooth film. Such films rapidly disintegrate in aqueous media at a rate that is independent of pH and film thickness.

A protective coating layer (i.e., seal coat) may be applied, if desired, by conventional coating techniques such as pan coating or fluid bed coating using solutions of polymers in water or suitable organic solvents or by using aqueous polymer dispersions. Suitable materials for the protective layer include cellulose derivatives such as hydroxyethyl cellulose, hydroxypropyl cellulose, hydroxypropyl methylcellulose, polyvinylpyrrolidone, polyvinylpyrrolidone/vinyl acetate copolymer, ethyl cellulose aqueous dispersions and the like. The protective coating layer may include antioxidants, chelating agents, colors or dyes.

A delayed release or enteric coating layer may be applied onto the capsule itself, or onto other coatings on the capsule, with or without seal coating, by conventional coating techniques, such as pan coating or fluid bed coating using solutions of polymers in water or suitable organic solvents or by using aqueous polymer dispersions. All commercially available pH-sensitive polymers are included. The API is not released in the acidic stomach environment of approximately below pH 4.5, but not limited to this value. The pharmaceutical active should become available when the pH-sensitive layer dissolves at the greater pH; after a certain delayed time; or after the unit passes through the stomach. If utilized, the preferred delay time is in the range of two to six hours.

Delayed release or enteric polymers include cellulose acetate phthalate, Cellulose acetate trimellitate, hydroxypropyl methylcellulose phthalate, polyvinyl acetate phthalate, carboxymethylethylcellulose, co-polymerized methacrylic acid/methacrylic acid methyl esters such as, for instance, materials known under the trade name EUDRAGIT L12.5, L100, or EUDRAGIT S12.5, S100 or similar compounds used to obtain enteric coatings. Aqueous colloidal polymer dispersions or re-dispersions can be also applied, e.g. EUDRAGIT L 30D-55, EUDRAGIT L100-55, EUDRAGIT S100, EUDRAGIT preparation 4110D (Rohm Pharma); AQUATERIC, AQUACOAT CPD 30 (FMC); KOLLICOAT MAE 30D and 30DP (BASF); EASTACRYL 30D (Eastman Chemical).

A sustained release film coat may include, but is not limited to, a water insoluble material such as a wax or a wax-like substance, fatty alcohols, shellac, zein, hydrogenated vegetable oils, water insoluble celluloses, polymers of acrylic and/or methacrylic acid, and any other slowly digestible or dispersible solids known in the art. The solvent for the hydrophobic coating material may be organic or aqueous. Preferably, the hydrophobic polymer is selected from (i) a water insoluble cellulosic polymer, such as an alkylcellulose, preferably ethylcellulose; (ii) an acrylic polymer; or (iii) mixtures thereof. In other preferred embodiments of the present invention, the hydrophobic material comprising the controlled release coating is an acrylic polymer. Any acrylic polymer which is pharmaceutically acceptable can be used for the purposes of the present invention. The acrylic polymers may be cationic, anionic or non-ionic polymers and may be acrylates, methacrylates, formed of methacrylic acid or methacrylic acid esters. Examples of suitable acrylic polymers include but are not limited to acrylic acid and methacrylic acid copolymers, methacrylic acid copolymers, methyl methacrylate copolymers, ethoxyethyl methacrylates, cynaoethyl methacrylate, methyl methacrylate, copolymers, methacrylic acid copolymers, methyl methacrylate copolymers, methyl methacrylate copolymers, methyl methacrylate copolymers, methacrylic acid copolymer, aminoalkyl methacrylate copolymer, methacrylic acid copolymers, methyl methacrylate copolymers, poly(acrylic acid), poly(methacrylic acid, methacrylic acid alkylamine copolymer, poly(methyl methacrylate), poly(methacrylic acid) (anhydride), methyl methacrylate, polymethacrylate, methyl methacrylate copolymer, poly(methyl methacrylate), poly(methyl methacrylate) copolymer, polyacrylamide, aminoalkyl methacrylate copolymer, poly(methacrylic acid anhydride), and glycidyl methacrylate copolymers.

A barrier coat may be included between the capsule and an outer coat, between outer coats, or on the outermost coat. The barrier coat may be comprised of an enteric or delayed release coat (as above) or a barrier (non-functional) layer, which serves as a protective coat and/or scavenger to prevent leaching from the shell (e.g., glycerol or water) to the outer API component or vice versa. For example, in some embodiments a barrier coat may be used to prevent leaching of glycerol and/or water inside the shell into the second API.

Embodiments of the invention may also include one or more coatings on the capsule comprising one or more sequestrants, such as but not limited to, citric acid, citric acid monohydrate, dibasic sodium phosphate, phosphoric acid, potassium citrate, sodium citrate dihydrate, and the like, and/or one or more scavengers, such as but not limited to, salts or polymers preferably having ester and/or carboxylic acid groups, as known to those of skill in the art.

In some embodiments of the invention, a single API is split into first and second API, with one portion disposed in the capsule and the second portion disposed on the capsule in one or more coatings. In other embodiments, a first API is disposed in the capsule and a second API, different from the first API, is disposed on the capsule in one or more coatings.

In some embodiments, the dosage form may be provided with a lag time between the administration of the first portion and the administration of the second portion, e.g., by a delayed release or enteric coating provided as a barrier layer. In other embodiments, there is an immediate release of the first portion of the API, followed by a delayed or sustained release of the second (and/or further) portion of the API. In further embodiments, there is a delayed release of the first portion, followed by a bolus of the second (and/or further) portion.

In some preferred embodiments of the present invention, there is at least one additional coating between the capsule and the at least one coating comprising the at least one second API, selected from the group consisting of immediate release coatings, protective coatings, enteric or delayed release coatings, sustained release coatings, barrier coatings, and combinations thereof.

Some preferred embodiments have at least one top coating on the coating comprising the at least one second API, selected from the group consisting of immediate release coatings, protective coatings, enteric or delayed release coatings, sustained release coatings, barrier coatings, and combinations thereof.

In some embodiments, the hard or soft capsule comprising the first API is optionally coated with at least one barrier coating and/or enteric or delayed release coating, which is then coated with the at least one coating containing the second API, same or different as the first API, which is then optionally coated with at least one top coating which is an enteric or delayed release coating and/or a seal coating.

While coating technology is used extensively in the pharmaceutical industry, e.g. for the application of functional or non-functional coats to single dosage forms and for the deposition of APIs onto sugar beads, there are several challenges which can be encountered during coating of soft gelatin capsules. These challenges are often attributed to the properties of gelatin and the dosage form. Soft capsules, such as soft gelatin capsules, generally contain a medicament dissolved or dispersed in oils or hydrophilic liquids (fill liquid). The inherent flexibility of the soft capsule is due to the presence of plasticizers and residual moisture in the capsule shell. Thus, soft capsules are a more dynamic system than conventional tablets or hard capsules. Atmospheric moisture or oxygen may permeate into the capsule shell or into the fill liquid. The drug or fill liquid may migrate into the capsule shell, while the plasticizer or residual water gelatin can potentially migrate into the fill liquid. Volatile components in soft capsules may escape into the atmosphere. Any of these negative aspects are avoided in accordance with the present invention.

As noted above, polymeric coatings are generally applied as aqueous-based solutions, organic-based solutions or dispersions, in which polymer-containing droplets are atomized with air or an inert gas and sprayed onto the substrate. Heated air or an inert gas may be added to the coating equipment to facilitate evaporation of the solvent and film formation. In the case of soft gelatin capsules, the processing parameters of spray rate and bed temperature must be controlled. Because gelatin is soluble in water, spraying an aqueous-based polymeric material at a high rate could lead to solubilization of the gelatin and capsule agglomeration. A high bed temperature may result in the evaporation of residual water from the capsule shell, causing the capsule to become brittle. Therefore, embodiments of the present invention comprises a method of coating soft gelatin capsules in which these consequences are avoided.

In addition, the deposition of the second API onto the surface of the soft capsules with high degree of accuracy could be affected by several factors. The accuracy of deposition needs to be demonstrated by evaluating coating uniformity which includes the mass variance of the coated capsules and the variance of the content of the coated second API.

In general, "uniformity of dosage unit" is defined as the degree of uniformity in the amount of the drug substance among dosage units (i.e., capsules). The uniformity of dosage unit can be demonstrated by, for example, the content uniformity method or the weight variation method, as appropriate. For example, the content uniformity method is based upon an assay of the individual content of drug substance(s) in a number of individual dosage units to determine whether the individual content is within the limits set. See, for example, USP 30 <905> "Uniformity of Dosage Units" pages 378-382, which is incorporated by reference herein in its entirety. In embodiments of the present invention, content uniformity of an active ingredient (i.e., either or both of the first API and the second API, preferably at least the second API) is within about 15% or less of the intended dosage, preferably within about 10% or less of the intended dosage, and more preferably within about 6% or less of the intended dosage. Content uniformity of an active ingredient is preferably controlled within a factor of about 15% or less between capsules, more preferably within a factor of about 10% or less, and even more preferably within a factor of about 6% or less between capsules.

Embodiments of the present invention provide for a method of coating a hard or soft capsule comprising the first API, with at least one coating comprising a second API, the method comprising controlling the rate of coating deposition on the soft gelatin capsule and controlling the temperature during the coating process to produce a physically and chemically stable coated soft gelatin capsule. This method also allows for a content uniformity of the second API of about 15% or less of the intended dose, preferably about 6% or less of the intended dose. The coating(s) of embodiments of the present invention may also be applied onto a tablet or other conventional pharmaceutical substrate.

Other embodiments of the present invention provide for a method of administering a hard or soft capsule in accordance with the invention to a subject for treatment of any of the diseases or conditions for which the API(s) may be used. For example, when the first API and/or the second API comprises a lipid regulation agent, the method of administration may include treatment of at least one condition or disease independently selected from the group consisting of hypertriglyceridemia, hypercholesterolemia, mixed dyslipidemia, coronary heart disease (CHD), vascular disease, atherosclerotic disease and related conditions.

Example 1

Omega-3 Fatty Acids and Simvastatin 1000 mg of K85EE (OMACOR®), an oil containing omega-3 fatty acids in ethyl ester form, is contained in a soft gelatin capsule. A barrier coating, a drug coating containing 20 mg of simvastatin combined with a coating material, and a top coat are sprayed onto the soft gelatin capsule, while controlling the rate of coating deposition and controlling the temperature during the coating process to produce a physically and chemically stable coated soft gelatin capsule.

The soft gelatin capsule is coated with a barrier coating from a solution of one or more polymers (e.g., hydroxypropylcellulose and/or ethyl cellulose), and optionally talc in an organic solvent (e.g., dehydrated alcohol USP 200 Proof).

The capsules are dried under vacuum in an oven at 40° C.±5° C. for at least 18 hours. The dried capsules are coated with a drug coating solution containing simvastatin and other coating ingredients, such as a film forming material (e.g., a polymer and/or binder), and an organic solvent, and then dried under vacuum at 40° C.±5° C. for at least 18 hours.

The dried drug coated capsules are coated with a top coat of a solution containing hydroxypropylcellulose, talc, BHA, and BHT in an organic solvent (e.g., dehydrated alcohol USP 200 proof), and dried under vacuum in an oven at 40° C.±5° C. for at least 18 hours.

In some embodiments, the dried simvastatin coated OMACOR®soft gelatin capsules are packaged in 200 cc white round wide mouth high density polyethylene (HDPE) bottles containing a dessicant (e.g., 2 g 4 A molecular sieve dessicant packet) and sealed with 38 MM white CRC caps.

Example 2

Stability and Dissolution of 20 mg/1000 mg Simvastatin Coated OMACOR® Soft Gelatin Capsules Simvastatin coated OMACOR® soft gelatin capsules were prepared as in Example 1, with a barrier coating that did not contain talc. Table 1 and FIG. 1 show the dissolution rate of simvastatin at 40° C. and 75% RH. Tables 2-4 show the stability over six months under different temperatures and relative humidities.

TABLE 1

| Dissolution of Simvastatin at 40° C./75% RH | | | | | |
|---|---|---|---|---|---|
| Interval | Initial | 4 weeks | 7 weeks | 3 months | 6 months |
| 15 minutes | 46 | 44 | 56 | 41 | 46 |
| 30 minutes | 77 | 85 | 86 | 78 | 82 |
| 45 minutes | 92 | 102 | 97 | 94 | 93 |
| 60 minutes | 96 | 107 | 102 | 102 | 97 |

TABLE 2

| Stability at 40° C./75% RH | | | | | | | |
|---|---|---|---|---|---|---|---|
| Stability Interval | Initial | 1 week | 2 weeks | 4 weeks | 7 weeks | 3 months | 6 months |
| Simvastatin Assay (% LC) | 106.3 | 104.6 | 106.3 | 103.9 | 103.3 | 100.4 | 101.7 |
| Simvastatin Degradants (%) | | | | | | | |
| Glycerol-Simvastatin Adduct (RRT 0.53) | <0.1 | <0.1 | 0.2 | 0.3 | 0.5 (0.54) | 0.7 (0.71) | 0.9 (0.89) |
| Impurity A | <0.1 | <0.1 | <0.1 | <0.1 | <0.1 | 0.1 (0.11) | 0.5 (0.49) |
| Impurity C | 0.1 | 0.1 | 0.2 | 0.2 | 0.2 | 0.3 (0.25) | 0.4 (0.36) |
| Ethyl Ester Simvastatin (RRT 1.44) | <0.1 (ND) | <0.1 (ND) | <0.1 (ND) | <0.1 (ND) | <0.1 (ND) | <0.1 (ND) | <0.1 (0.04) |
| TOTAL Known Simvastatin Degradants | 0.1 | 0.1 | 0.2 | 0.4 | 0.8 | 1.1 (1.17) | 1.8 (1.78) |

TABLE 3

| Stability at 30° C./65% RH | | | | |
|---|---|---|---|---|
| Stability Interval | Initial | 2 months | 3 months | 6 months |
| Simvastatin Assay (% LC) | 106.3 | 102.0 | 100.2 | 99.9 |
| Simvastatin Degradants (%) | | | | |
| Glycerol-Simvastatin Adduct (RRT 0.53) | <0.1 | 0.2 (0.18) | 0.3 (0.26) | 0.4 (0.40) |

TABLE 3-continued

Stability at 30° C./65% RH

| Stability Interval | Initial | 2 months | 3 months | 6 months |
|---|---|---|---|---|
| Impurity A | <0.1 | <0.1 | <0.1 (0.04) | <0.1 (0.09) |
| Impurity C | 0.1 | 0.1 | 0.2 (0.16) | 0.2 (0.22) |
| Ethyl Ester | <0.1 | <0.1 | <0.1 | <0.1 |
| Simvastatin (RRT 1.44) | (ND) | (ND) | (ND) | (0.03) |
| TOTAL Known Simvastatin Degradants | 0.1 | 0.2 | 0.5 (0.46) | 0.6 (0.74) |

TABLE 4

Stability at 25° C./60% RH

| Stability Interval | Initial | 3 months | 4.5 months | 6 months |
|---|---|---|---|---|
| Simvastatin Assay (% LC) | 106.3 | 103.9 | 97.3 | 100.9 |
| Simvastatin Degradants (%) | | | | |
| Glycerol-Simvastatin Adduct (RRT 0.53) | <0.1 | 0.1 (0.13) | 0.2 (0.17) | 0.2 (0.21) |
| Impurity A | <0.1 | <0.1 (0.03) | <0.1 (0.05) | <0.1 (0.05) |
| Impurity C | 0.1 | 0.1 (0.14) | 0.2 (0.20) | 0.2 (0.18) |
| Ethyl Ester | <0.1 | <0.1 | <0.1 | <0.1 |
| Simvastatin (RRT 1.44) | (ND) | (ND) | (0.03) | (0.03) |
| TOTAL Known Simvastatin Degradants | 0.1 | 0.2 (0.27) | 0.4 (0.40) | 0.4 (0.47) |

Example 3

Omega-3 Fatty Acids and Fenofibrate 1000 mg of K85EE, an oil containing omega-3 fatty acids in ethyl ester form, is contained in a soft gelatin capsule. 5-100 mg of fenofibrate is combined with a coating material, such as a film forming material and/or binder, and the composition is sprayed onto the soft gelatin capsule, while controlling the rate of coating deposition and controlling the temperature during the coating process to produce a physically and chemically stable coated soft gelatin capsule. Optionally, one or more enteric coats are placed between the fenofibrate coating layer and the soft gelatin capsule to provide a delayed release of the omega-3 fatty acid ethyl esters.

Example 4

Fenofibrate and Pravastatin 5-200 mg of fenofibrate is contained in a soft gelatin capsule in a pharmaceutically acceptable vehicle. 2-80 mg of pravastatin is combined with a coating material, such as a film forming material and/or binder, and the composition is coated onto the soft gelatin capsule by pan coating. The rate of coating deposition and the temperature are controlled during the coating process to produce a physically and chemically stable coated soft gelatin capsule. A top coat is optionally applied.

Example 5

Omega-9 Fatty Acids and Propranolol 500-1500 mg of an oil containing omega-9 fatty acids is contained in a soft gelatin capsule. 10-160 mg of propranolol is combined with a coating material, such as a film forming material and/or binder, and the composition is coated onto the soft gelatin capsule by fluid bed coating. The rate of coating deposition and the temperature are controlled during the coating process to produce a physically and chemically stable coated soft gelatin capsule. Optionally, one or more enteric coats are placed between the propranolol coating layer and the soft gelatin capsule to provide a delayed release of the omega-9 fatty acids.

Example 6

Omega-3 Fatty Acid Ethyl Esters and Enalapril 500-1500 mg of an oil containing a 35% concentration of omega-3 fatty acids is contained in a soft gelatin capsule. 2.5-20 mg of enalapril is combined with a coating material, such as a film forming material and/or binder, and the composition is sprayed onto the soft gelatin capsule by spray coating. The rate of coating deposition and the temperature are controlled during the coating process to produce a physically and chemically stable coated soft gelatin capsule. A top coat is optionally applied.

Example 7

Omega-3 Fatty Acid Ethyl Esters and Pioglitazone 1000 mg of K85EE (OMACOR®), an oil containing omega-3 fatty acids in ethyl ester form, is contained in a hard capsule. 10-200 mg of pioglitazone is combined with a coating material, such as a film forming material and/or binder, and the composition is coated onto the hard capsule by fluid bed coating, while controlling the rate of coating deposition and controlling the temperature during the coating process to produce a physically and chemically stable coated hard capsule. A non-functional barrier coat is placed between the drug coat layer and the hard gelatin capsule to prevent leaching of the first API to the second API or vice versa, and/or to prevent leaching of capsular materials (e.g., glycerol) into the first API and/or second API.

Throughout this application, various patents and publications have been cited. The disclosures of these patents and publications in their entireties are hereby incorporated by reference into this application, in order to more fully describe the state of the art to which this invention pertains.

The invention is capable of considerable modification, alteration, and equivalents in form and function, as will occur to those ordinarily skilled in the pertinent arts having the benefit of this disclosure.

While the present invention has been described for what are presently considered the preferred embodiments, the invention is not so limited. To the contrary, the invention is intended to cover various modifications and equivalent arrangements included within the spirit and scope of the detailed description provided above. Therefore, the scope of the appended claims should be accorded the broadest interpretation so as to encompass all such modification.

We claim:

1. A pharmaceutical composition in unit dose form comprising:

(a) a soft gelatin capsule comprising a single, first active pharmaceutical ingredient ("API"), wherein the first API is an omega-3 fatty acid oil and is present in the form of a pharmaceutically acceptable vehicle;

(b) one or more coatings on the capsule, wherein at least one coating comprises a second active pharmaceutical ingredient ("API"), wherein the second API is a statin compound and is the only API in the one or more coatings, and wherein the at least one coating comprising the second active pharmaceutical ingredient is applied by pan coating, fluid bed coating, or spray coating; and wherein the unit dose form is a pharmaceutical grade finished dosage form suitable for oral administration.

2. The pharmaceutical composition of claim 1, further comprising at least one additional coating between the capsule and the at least one coating comprising the second active pharmaceutical ingredient.

3. The pharmaceutical composition of claim 2, wherein the at least one additional coating is selected from the group consisting of immediate release coatings, protective coatings, enteric or delayed release coatings, sustained release coatings, barrier coatings, and combinations thereof.

4. The pharmaceutical composition of claim 1, further comprising at least one top coating on the at least one coating comprising the second active pharmaceutical ingredient.

5. The pharmaceutical composition of claim 4, wherein the at least one top coating is selected from the group consisting of immediate release coatings, protective coatings, enteric or delayed release coatings, sustained release coatings, barrier coatings, and combinations thereof.

6. The pharmaceutical composition of claim 1, further comprising at least one barrier coating between the capsule and the at least one coating comprising the second active pharmaceutical ingredient, and at least one top coating selected from the group consisting of enteric or delayed release coatings, protective coatings, and combinations thereof, on the at least one coating comprising the second active pharmaceutical ingredient.

7. The pharmaceutical composition of claim 1, wherein the capsule has an oblong shape.

8. The pharmaceutical composition of claim 1, wherein the at least one coating comprising the second active pharmaceutical ingredient comprises at least one compound present in an amount sufficient to prevent oxidative degradation of the second active pharmaceutical ingredient for a pharmaceutically acceptable duration of time.

9. The pharmaceutical composition of claim 1, wherein the at least one coating comprising the second active pharmaceutical ingredient has a thickness sufficient to prevent oxidative degradation of the second active pharmaceutical ingredient for a pharmaceutically acceptable duration of time.

10. A method of treating a condition or disease independently selected from the group consisting of hypertriglyceridemia, hypercholesterolemia, mixed dyslipidemia, coronary heart disease (CHD), vascular disease, and atherosclerotic disease, comprising administering to the subject the pharmaceutical composition of claim 1.

11. The pharmaceutical composition of claim 1 wherein the omega-3 fatty acid oil comprises EPA, DHA, a triglyceride of EPA, a triglyceride of DHA, EPA ethyl ester, DHA ethyl ester, or a mixture thereof.

12. The pharmaceutical composition of claim 11 wherein the omega-3 fatty acid oil comprises EPA ethyl ester and DHA ethyl ester.

13. The pharmaceutical composition of claim 11 wherein the omega-3 fatty acid oil comprises at least 80% EPA and DHA, about 40% to about 55% EPA, and about 30% to about 60% DHA, in an EPA:DHA weight ratio of from 1:2 to 2:1, and wherein the percentage by weight is based on the total fatty acid content in the capsule and on the ethyl ester form of the fatty acids.

14. The pharmaceutical composition of claim 13 wherein the EPA and DHA are in the ethyl ester form.

15. The pharmaceutical composition of claim 1 wherein the statin compound is selected from pitavastatin, pravastatin, simvastatin, lovastatin, atorvastatin, and fluvastatin.

16. The pharmaceutical composition of claim 11 wherein the statin compound is selected from pitavastatin, pravastatin, simvastatin, lovastatin, atorvastatin, and fluvastatin.

17. The pharmaceutical composition of claim 14 wherein the statin compound is selected from pitavastatin, pravastatin, simvastatin, lovastatin, atorvastatin, and fluvastatin.

18. The pharmaceutical composition of claim 14 wherein the statin compound is simvastatin.

19. The pharmaceutical composition of claim 1, wherein the capsule further comprises a solubilizer.

20. The pharmaceutical composition of claim 14, wherein the capsule further comprises a solubilizer.

21. The pharmaceutical composition of claim 18, wherein the capsule further comprises a solubilizer.

\* \* \* \* \*